United States Patent

Reichardt et al.

Patent Number: 5,981,561
Date of Patent: Nov. 9, 1999

[54] FUNGICIDE MIXTURES

[75] Inventors: Michael Reichardt, Kallstadt; Reinhold Saur, Böhl-Iggelheim; Klaus Schelberger, Gönnheim; Eberhard Ammermann, Heppenheim; Gisela Lorenz, Neustadt; Siegfried Strathmann, Limburgerhof, all of Germany

[73] Assignee: BASF Aktiengesellschaft, Ludwigshafen, Germany

[21] Appl. No.: 09/029,993

[22] PCT Filed: Sep. 4, 1996

[86] PCT No.: PCT/EP96/03887

§ 371 Date: Jun. 1, 1998

§ 102(e) Date: Jun. 1, 1998

[87] PCT Pub. No.: WO97/09880

PCT Pub. Date: Mar. 20, 1997

[30] Foreign Application Priority Data

Sep. 13, 1995 [DE] Germany .................. 795 33 196

[51] Int. Cl.[6] ............... A01N 37/34; A01N 43/64
[52] U.S. Cl. ............................ 514/383; 514/525
[58] Field of Search ..................... 514/383, 525

[56] References Cited

U.S. PATENT DOCUMENTS

| H1400 | 1/1995 | Culbreath et al. | 514/383 |
|---|---|---|---|
| 4,652,580 | 3/1987 | Janssen et al. | 514/383 |
| 4,906,652 | 3/1990 | Karbach et al. | 514/383 |

FOREIGN PATENT DOCUMENTS

| 2 940 | 7/1979 | European Pat. Off. . |
| 196 038 | 10/1986 | European Pat. Off. . |
| 43 09 272 | 9/1994 | Germany . |
| 2 267 644 | 12/1993 | United Kingdom . |

OTHER PUBLICATIONS

BAS 490 F, Fungicide, 68, Evironmental Fate, The Pesticide Manual, 10th Ed. (1994).
132 Chlorothalonil, Fungicide, 193–194, Evironmental Fate, The Pestcide Manual, 10th Ed. (1994) (Tomlin).

*Primary Examiner*—Allen J. Robinson
*Attorney, Agent, or Firm*—Keil & Weinkauf

[57] ABSTRACT

A fungicidal mixture comprising
  a) (2RS,3SR)-1-[3-(2-chlorophenyl)-2,3-epoxy-2-(4-fluorophenyl)-propyl]-1H-1,2,4-triazole

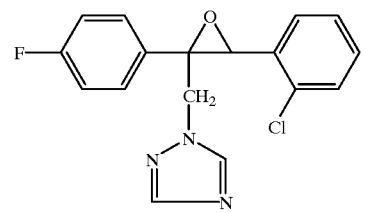
(I)

or a salt or adduct thereof, and
  b) tetrachloroisophthalonitrile II

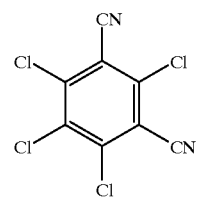
(II)

in a synergistically active amount, and its use for controlling harmful fungi.

6 Claims, No Drawings

FUNGICIDE MIXTURES

This application is a 371 of PCT/EP96/03887, filed Sep. 4, 1996.

The present invention relates to a fungicidal mixture which comprises
   a) (2RS,3SR)-1-[3-(2-chlorophenyl)-2,3-epoxy-2-(4-fluorphenyl)propyl]-1H-1,2,4-triazole

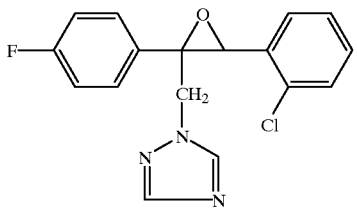

(I)

or a salt or adduct thereof, and
   b) tetrachloroisophthalonitrile II

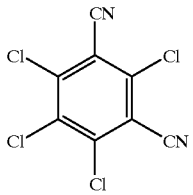

(II)

in a synergistically active amount.

The invention furthermore relates to methods of controlling harmful fungi using mixtures of the compounds I and II and to the use of compound I and of the compound II for the preparation of such mixtures.

The compound of the formula I, its preparation and its action against harmful fungi are disclosed in EP-A 196 038 and "The Pesticide Manual", 10th Edition, The British Crop Protection Council and The Royal Society of Chemistry, 1994—termed "Pesticide Manual" hereinbelow—Page 67: BAS 480 F, proposed common name: epoxiconazole). The compound II (common name: chlorothalonil), its preparation and its action against harmful fungi is also known (cf. "Pesticide Manual", Page 193).

With a view to reducing the rate of application and to improving the spectrum of action of the known compounds I and II, it is an object of the present invention to provide mixtures which have an improved activity against harmful fungi while the total amount of active ingredients applied is reduced (synergistic mixtures).

Accordingly, we have found that this object is achieved by the mixture defined at the outset. Moreover, we have found that better control of the harmful fungi is possible by applying compound I and compound II simultaneously, together or separately, or by applying compound I and compound II in succession than when the individual compounds are used alone.

Due to the basic character of the 1,2,4-triazole ring group, the compound I is capable of forming salts or adducts with inorganic or organic acids or with metal ions.

Examples of inorganic acids are hydrohalic acids such as hydrofluoric acid, hydrochloric acid, hydrobromic acid and hydriodic acid, furthermore carbonic acid, sulfuric acid, phosphoric acid and nitric acid.

Suitable organic acids are, for example: formic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals having 1 to 20 carbon atoms), arylsulfonic acids or aryldisulfonic acids (aromatic radicals such as phenyl and naphthyl which have attached to them one or two sulfo groups), alkylphosphonic acids (phosphonic acids having straight-chain or branched alkyl radicals of 1 to 20 carbon atoms), arylphosphonic acids or aryldiphosphonic acids (aromatic radicals such as phenyl and naphthyl which have attached to them one or two phosphoric acid radicals), it being possible for the alkyl or aryl radicals to have attached to them further substituents, eg. p-toluenesulfonic acid, salicylic acid, p-aminosalicylic acid, 2-phenoxybenzoic acid, 2-acetoxybenzoic acid etc.

Suitable metal ions are, in particular, the ions of the elements of the first to eighth sub-group, mainly chromium, manganese, iron, cobalt, nickel, copper, zinc, and also of the second main group, mainly calcium and magnesium, of the third and fourth main groups, in particular aluminum, tin and lead. The metals can exist in the various valencies which they can assume.

When preparing the mixtures, it is preferred to employ the pure active ingredients I and II, with which further active ingredients against harmful fungi or other pests such as insects, arachnids or nematodes, or else herbicidal or growth-regulating active ingredients, or fertilizers, can be admixed, if so required.

The mixtures of the compounds I and II, or the simultaneous joint or separate use of the compounds I and II, have an outstanding action against a wide spectrum of phytopathogenic fungi, in particular from the classes of the Ascomycetes, Basidiomycetes, Phycomycetes and Deuteromycetes. Some of them act systemically and can therefore also be employed as foliar- and soil-acting fungicides.

They are especially important for controlling a large number of fungi in a variety of crop plants such as cotton, vegetable species (eg. cucumbers, beans and cucurbits), barley, grass, oats, coffee, corn, fruit species, rice, rye, soybean, grape vine, wheat, ornamentals, sugar cane and a variety of seeds.

They are particularly suitable for controlling the following phytopathogenic fungi: *Erysiphe graminis* (powdery mildew) on cereals, *Erysiphe cichoracearum* and *Sphaerotheca fuliginea* on cucurbits, *Podosphaera leucotricha* on apples, *Uncinula necator* on grape vines, Puccinia species on cereals, Rhizoctonia species on cotton, rice and lawns, Ustilago species on cereals and sugar cane, *Venturia inaequalis* (scab) on apples, Helminthosporium species on cereals, Septoria nodorum on wheat, *Botrytis cinera* (gray mold) on strawberries and grape vines, *Cercospora arachidicola* on groundnuts, *Pseudocercosporella herpotrichoides* on wheat and barley, *Pyricularia oryzae* on rice, *Phytophthora infestans* on potatoes and tomatoes, *Plasmopara viticola* on grape vines, Alternaria species on vegetables and fruit, and Fusarium and Verticillium species.

Furthermore, they can be used in the protection of materials (eg. in the protection of wood), for example against *Paecilomyces variotii*.

The compounds I and II can be applied simultaneously together or separately or in succession, with the order, in the case of separate application, generally not having any effect on the result of the control measures.

The compounds I and II are usually used in a weight ratio of 10:1 to 0.05:1, preferably 5:1 to 0.1:1, in particular 3:1 to 0.2:1.

The application rates of the mixtures according to the invention are, especially on agricultural land, from 0.01 to 3 kg/ha, preferably 0.1 to 1.5 kg/ha, in particular 0.1 to 1.0 kg/ha, depending on the nature of the desired effect. In the case of compound I, the application rates are from 0.01 to 0.5 kg/ha, preferably 0.05 to 0.5 kg/ha, in particular 0.05 to 0.4 kg/ha. Accordingly, in the case of the compounds II [sic], the application rates are from 0.01 to 2 kg/ha, preferably 0.05 to 1 kg/ha, in particular 0.05 to 0.5 kg/ha.

For seed treatment, application rates of the mixture are generally from 0.001 to 50 g/kg of seed, preferably 0.01 to 10 g/kg, in particular 0.01 to 8 g/kg.

If phytopathogenic harmful fungi are to be controlled, the separate or joint application of the compounds I and II or of the mixtures of the compounds I and II is effected by spraying or dusting the seeds, the plants or the soils before or after sowing of the plants, or before or after plant emergence.

The fungicidal synergistic mixtures according to the invention, or the compounds I and II, can be formulated for example in the form of ready-to-spray solutions, powders and suspensions or in the form of highly concentrated aqueous, oily or other suspensions, dispersions, emulsions, oil dispersions, pastes, dusts, materials for spreading or granules, and applied by spraying, atomizing, dusting, spreading or pouring. The use form depends on the intended purpose; in any case, it should guarantee as fine and uniform as possible a distribution of the mixture according to the invention.

The formulations are prepared in a manner known per se, eg. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols or of fatty alcohol glycol ethers, condensates of sulfonated naphthalene and its derivatives with formaldehyde, condensates of naphthalene, or of the naphthalenesulfonic acids, with phenol and formaldehyde, polyoxyethylene octylphenol ether, ethoxylated isooctyl-, octyl- or nonylphenol, alkylphenol, polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene ethers, lauryl alcohol polyglycol ether acetate, sorbitol esters, ligninsulfite waste liquors or methylcellulose.

Powders, materials for spreading and dusts can be prepared by mixing or jointly grinding the compounds I or II or the mixture of the compounds I and II with a solid carrier.

Granules (eg. coated granules, impregnated granules or homogeneous granules) are usually prepared by binding the active ingredient, or active ingredients, to a solid carrier.

Fillers or solid carriers are, for example, mineral earths, such as silica gels, silicas, silicates, talc, kaolin, limestone, lime, chalk, bole, loess, clay, dolomite, diatomaceous earth, calcium sulfate, magnesium sulfate, magnesium oxide, ground synthetic materials, and fertilizers such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise 0.1 to 95% by weight, preferably 0.5 to 90% by weight, of one of the compounds I and II or of the mixture of the compounds I and II. The active ingredients are employed in a purity of from 90% to 100%, preferably 95% to 100% (according to NMR or HPLC spectrum [sic]).

The compounds I and II, the mixtures, or the corresponding formulations, are applied by treating the harmful fungi, their environment, or the plants, seeds, soils, areas, materials or spaces to be kept free from them, with a fungicidally active amount of the mixture, or of the compounds I and II in the case of separate application.

Application can be effected before or after infection by the harmful fungi.

USE EXAMPLE

Activity Against Botrytis Cinerea

The active ingredients, separately or together, were formulated as a 10% strength emulsion in a mixture of 70% by weight of cyclohexanone, 20% by weight of Nekanil® LN (Lutensol® AP6, wetting agent having emulsifying and dispersing action, based on ethoxylated alkylphenols) and 10% by weight of Emulphor® EL (Emulan® EL, emulsifier based on ethoxylated fatty alcohols) and diluted with water to give the desired concentration.

Bell pepper seedlings cultivar "Neusiedler Ideal Elite" were grown until 4–5 leaves had developed properly and then sprayed to drip point with aqueous suspensions comprising 80% by weight of active ingredient and 20% by weight of emulsifier in the dry matter. After the spray coating had dried on, the plants were sprayed with a conidia suspension of the fungus Botrytis cinerea and placed into a chamber with high atmospheric humidity at 22–24° C. After 5 days, the disease on the untreated control plants had developed to such an extent that the leaf necroses formed covered the majority of the leaves.

For evaluation, the visually determined values for the percentage of diseased leaf area was converted into (observed) efficacies as a % of the untreated control.

The theoretically expected efficacies of the mixtures of the active ingredients were determined using Colby's formula [R. S. Colby, Weeds 15, 20–22 (1967)] and compared with the observed efficacies.

Colby's formula:

$$E = x + y - x \cdot y / 100$$

E expected efficacy, expressed in % of the untreated control, when using the mixture of two active ingredients A and B at the concentrations a and b x efficacy, expressed in % of the untreated control, when using active ingredient A at a concentration of a y efficacy, expressed in % of the untreated control, when using active ingredient B at a concentration of b An efficacy of 0 means that the infection level corresponds to the untreated control; an efficacy of 100 means an infection level of 0%.

Test results (untreated control: infection level 100%)

| Active ingredient | Concentration of active ingredient in the spray mixture | Efficacy in % of the untreated control |
|---|---|---|
| I: | 6 | 50 |
| Epoxiconazole | 3 | 40 |
|  | 1.5 | 10 |
| II: | 50 | 0 |
| Chlorothalonil | 12.5 | 0 |
|  | 6 | 0 |

-continued

| Mixtures of I + II [Ratio] | Observed Efficacy | Expected Efficacy* |
|---|---|---|
| 6 + 6 [1:1] | 72 | 50 |
| 3 + 3 [1:1] | 70 | 40 |
| 6.25 + 50 [1:8] | 92 | 50 |
| 1.5 + 12.5 [1:8] | 70 | 10 |

*) calculated using Colby's formula

The test results show that the observed efficacy for all mixing ratios is higher than the efficacy calculated using Colby's formula.

We claim:

1. A fungicidal mixture comprising a) a (2RS,3SR)-1-1H-1,2,4-triazole compound I

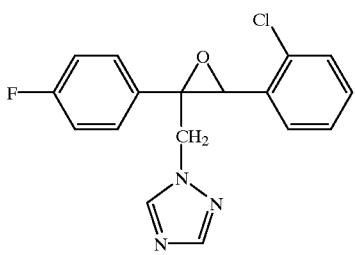

or a salt or adduct thereof, and b) a tetrachloroisophthalonitrile compound II

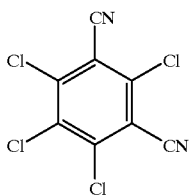

in a synergistically active amount.

2. The mixture defined in claim 1, wherein the weight ratio of the compound I or the salt or adduct thereof to the compound II is 10:1 to 0.05:1.

3. A method of controlling harmful fungi, which comprises treating the harmful fungi, their environment, or the plants, seeds, soils, areas, materials or spaces to be kept free from said fungi, with a synergistically effective amount of the compound I or the salt or adduct thereof as set forth in claim 1 and the compound II as set forth in claim 1.

4. The method of claim 3, wherein the compound I

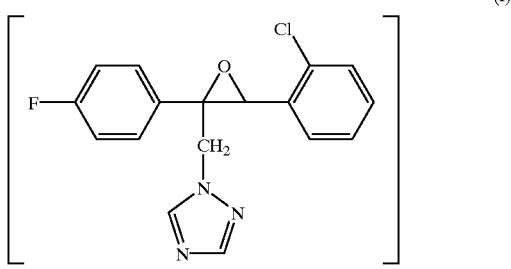

or the salt or adduct thereof and the compound II

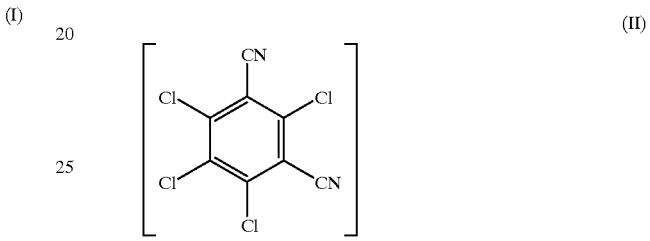

are applied simultaneously together or separately or in succession.

5. The method of claim 3, wherein 0.01 to 0.5 kg/ha of the compound I

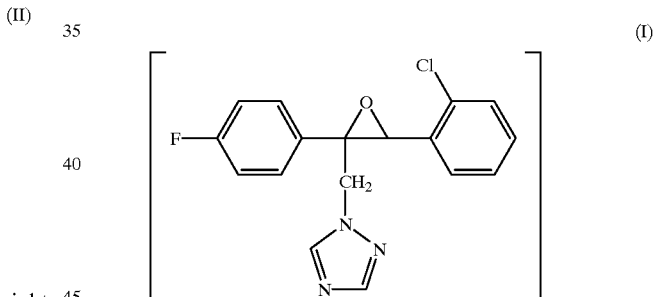

or the salt or adduct thereof are applied.

6. The method of claim 3, wherein 0.01 to 2 kg/ha of the compound II are applied.

* * * * *

UNITED STATES PATENT AND TRADEMARK OFFICE
CERTIFICATE OF CORRECTION

PATENT NO.: 5,981,561

DATED: November 9, 1999

INVENTOR(S): REICHARDT et al.

It is certified that error appears in the above-identified patent and that said Letters Patent is hereby corrected as shown below:

On the cover sheet, item [30], "795 33 196" should be --195 33 796--.

Col. 5, claim 1, second line, "(2RS.3SR)-1-1H-1.2.4-triazole" should be --(2RS.3SR)-1-[3-(2-chlorophenyl)-2,3-epoxy-2-(4-fluorophenyl)-propyl]-1H-1,2,4-triazole--.

Signed and Sealed this

Eighth Day of August, 2000

Attest:

Q. TODD DICKINSON

Attesting Officer

Director of Patents and Trademarks